United States Patent

Lin

[11] Patent Number: 5,927,984
[45] Date of Patent: Jul. 27, 1999

[54] BRIDGE HAVING PRE-FORMED TOOTH CROWNS CONNECTED VIA MALE AND FEMALE FASTENERS

[76] Inventor: Jyh-Sheng Lin, 184, Ching-Yun Rd., Tuu-Cherng, Taipei Hsien, R.O.C., Taiwan

[21] Appl. No.: 09/153,324

[22] Filed: Sep. 15, 1998

[51] Int. Cl.⁶ .................................................. A61C 5/08
[52] U.S. Cl. ........................................................ 433/218
[58] Field of Search .................................... 433/180, 181, 433/182, 183, 218, 219

[56] References Cited

U.S. PATENT DOCUMENTS

| 1,753,644 | 4/1930 | Burden | 433/181 |
| 3,530,582 | 9/1970 | Weissman | 433/219 |
| 4,431,418 | 2/1984 | Kienhofer | 433/183 |

FOREIGN PATENT DOCUMENTS

| 3604125 | 9/1987 | Germany | 433/219 |

*Primary Examiner*—Jeffrey A. Smith
*Attorney, Agent, or Firm*—Birch, Stewart, Kolasch & Birch, LLP

[57] ABSTRACT

A pre-formed tooth crown comprises a connection at the lateral surfaces capable of bridging three-tooth crowns. The connection further comprises a male fastener at one lateral surface and a female fastener at the opposing lateral surface, where the male fastener has a center hole and the female fastener has a corresponding central through hole. In order to form a crown bridge with at least three-tooth crowns, the male fastener of one tooth crown can engage with the female fastener of an adjacent tooth crown. While after the crown bridge is located onto the patient's teeth, a lining material stuffed inside the tooth crowns can be then squeezed from one tooth crown to an adjacent tooth crown via the center hole and the central through hole for ensuring the binding within the crown bridge.

12 Claims, 8 Drawing Sheets

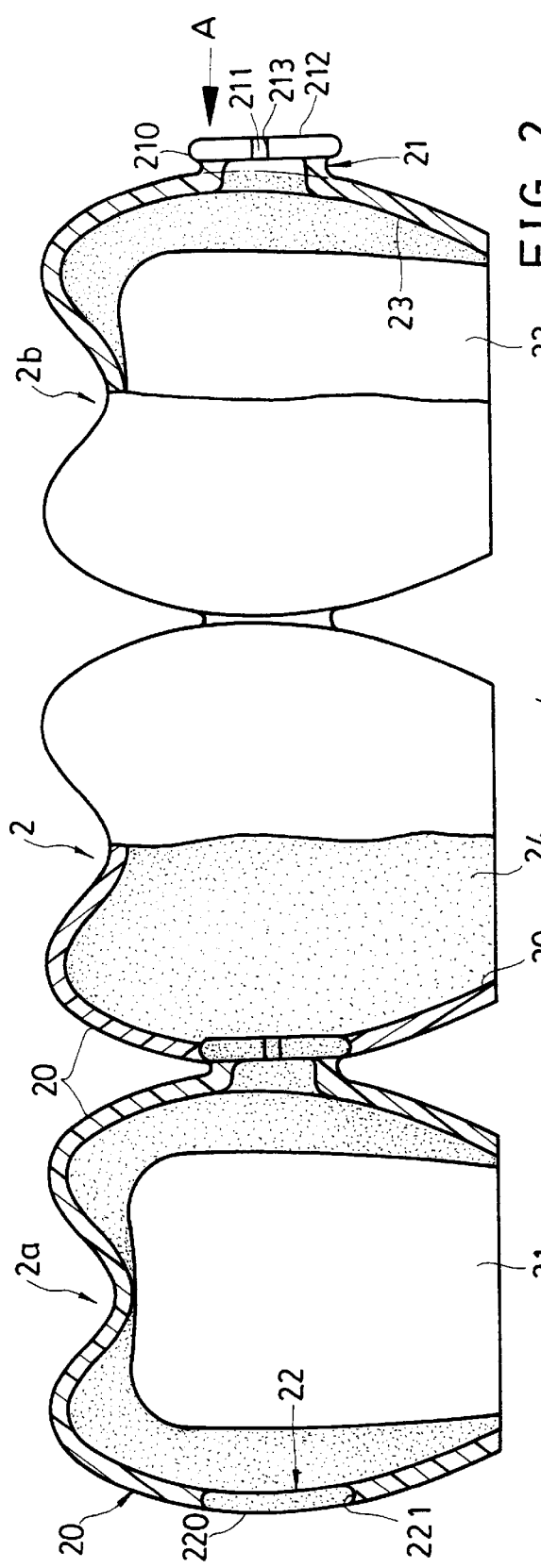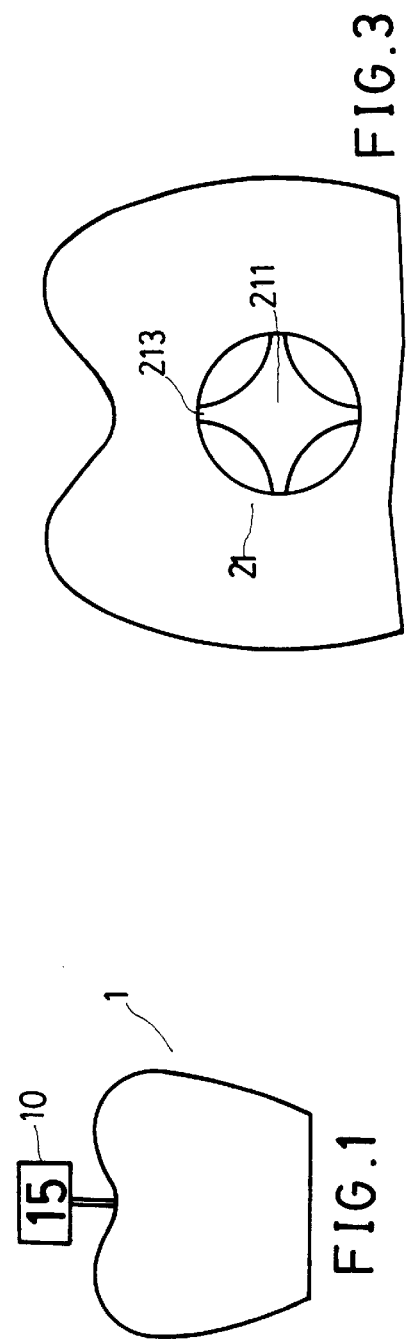

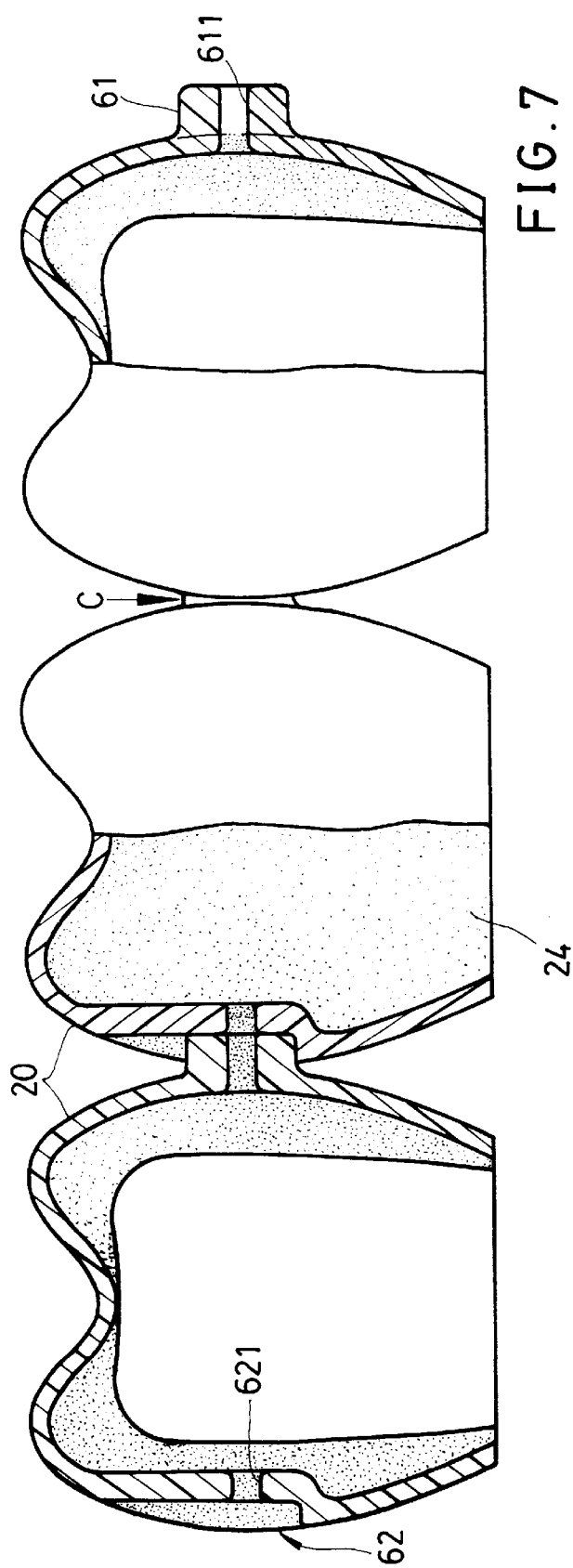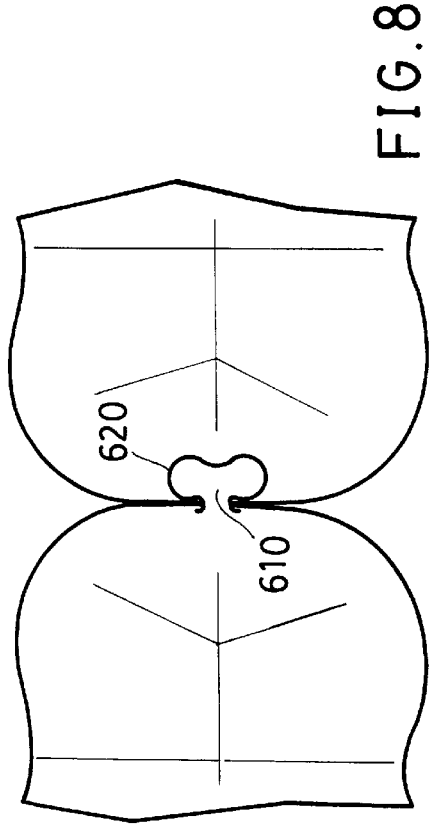

BRIDGE HAVING PRE-FORMED TOOTH CROWNS CONNECTED VIA MALE AND FEMALE FASTENERS

BACKGROUND OF THE INVENTION (1) Field of the Invention

The invention relates to a pre-formed tooth crown, and more particularly to which is designed for prosthesis in dentistry and can be easily used to construct a crown bridge by joining multiple tooth crowns.

(2) Description of the Prior Art

Prosthesis in dentistry is a crucial and professional therapy process, which can retrieve the normal teeth function by wearing a tooth restoration. However, during the therapy, the work in constructing a tooth restoration usually takes lots of time; for the work including the impression of a tooth profile, investment casting from the imitate profile by using metal or porcelain fused to metal to produce a tooth restoration, and finally the cementation of the tooth restoration. Normally, 7–10 working days are required for a complete therapy. In the meantime, the patient needs to wear a temporary tooth crown upon the abutment tooth to prevent any unexpected displacement and to perform a minimum chewing function. Such a tooth crown is needed and worn right after the abutment tooth is prepared. This temporary crown is made of resin and hardening glue, is prepared in the clinics by retrial and re-modified upon the abutment tooth, and is cemented by luting cement.

The work of forming an aforesaid resin crown is tedious and time-wasting. Therefore, a model crown as shown in FIG. 1 is promoted in the market. The model crowns 1 are manufactured in accordance variously with the profile and size of human teeth, incisors, premolars, and molars, and is numbered by a label 10. While using the model crowns, the dentist will firstly determine a proper model crown 1 according to patient's teeth condition, then set the model crown 1 by cement, finally cut the label 10 and polish.

Apparently, the usuage of the model crown 1 help the dentist away from the trivial process of forming a restoration, and provide the patient a more rapid dental therapy, especially saving a lot of time in keeping mouth open for retrying the restoration. However, this model crown 1 can only be applied to the patient with sick teeth, and is not applicable to patients with missing teeth. For the patient with a missing tooth, a temporary three-unit restoration bridge must be made in according to the extracted tooth and the adjacent teeth. At this situation, the model crown 1 is not useful, because the model crown 1 fails to have connection ability.

Therefore, an invention devoting to resolving the aforesaid disadvantages of the model crown or to the tooth restoration is necessary, definitely.

SUMMARY OF THE INVENTION

Accordingly, it is a primary object of the present invention to provide a pre-formed tooth crown which is particularly designed for prosthesis in dentistry and can be easily used to construct a crown bridge by joining multiple tooth crowns.

The preformed tooth crown in accordance with the present invention comprises a connection means at the lateral surfaces capable of bridging two tooth crowns. The connection means further comprises a male fastener at one lateral surface and a female fastener at the opposing lateral surface, where the male fastener has a center hole and the female fastener has a corresponding central through hole. In order to form a crown bridge with at least three-tooth crowns, the male fastener of one tooth crown can engage with the female fastener of adjacent tooth crown. While after the crown bridge is located onto the patient's teeth, a lining material stuffed inside the tooth crowns can be then squeezed from one tooth crown to adjacent tooth crown via the center hole and the central through hole for ensuring the binding within the crown bridge. Preferably, the male fastener is an isolated connector with two parallel side buttons and the female fastener located at both lateral surfaces is a cavity for receiving one of the side buttons of said male fastener while in engagement for forming a crown bridge.

Preferably, the male fastener is a hollow mushroom-shaped body rising above adjacent surface with a booming flower-shaped circumference and a central hole, and the female fastener is a receiving cavity for accommodating the male fastener of another tooth crown while in engagement for forming a crown bridge.

Preferably, the male fastener is a ball-shaped body with a booming flower-shaped circumference and a central hole, and the female fastener is a ball-shaped cavity for accommodating the male fastener of another tooth crown while in engagement for forming a crown bridge.

Preferably, the male fastener is a pipe-shaped body with a central hole, and the female fastener is a ring-shaped groove for accommodating the male fastener of another tooth crown while in engagement for forming a crown bridge.

Preferably, the male fastener is an 8-shaped key with a central hole, and the female fastener is an 8-shaped key way for accommodating the male fastener of another tooth crown while in engagement for forming a crown bridge.

Preferably, the male fastener is a cross button with a central hole, and the female fastener is a cross socket for accommodating the male fastener of another tooth crown while in engagement for forming a crown bridge.

Preferably, the male fastener is a pin with an upper central hole, and the female fastener is a pin hole for accommodating the male fastener of another tooth crown while in engagement for forming a crown bridge.

Preferably, the male fastener is a pair of round-head buttons with individual central holes, and the female fastener is a round cavity with surface through hole plate. The surface through hole plate further includes a pair of holes for allowing the round-head buttons to penetrate, and the round cavity is used for accommodating the round-head buttons of the male fastener of another tooth crown while in engagement for forming a crown bridge.

All these objects are achieved by the pre-formed tooth crown described below.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will now be specified with reference to its preferred embodiment illustrated in the drawings which are given by way of illustration only, and thus are not limitative of the present invention, and, in which FIG. 1 is a schematic view of the model crown known in the art.

FIG. 2 is a front portion sectional view of the first embodiment of the pre-formed tooth crown in accordance with the present invention.

FIG. 3 is a lateral view of the preferred pre-formed tooth crown in accordance with the present invention viewing from point A of FIG. 2.

FIG. 7 is a front portion sectional view of the fourth embodiment of the pre-formed tooth crown in accordance with the present invention.

FIG. 8 is a lateral view of the preferred pre-formed tooth crown in accordance with the present invention viewing from point C of FIG. 7.

DESCRIPTION OF THE PREFERRED EMBODIMENT

Figure 4:
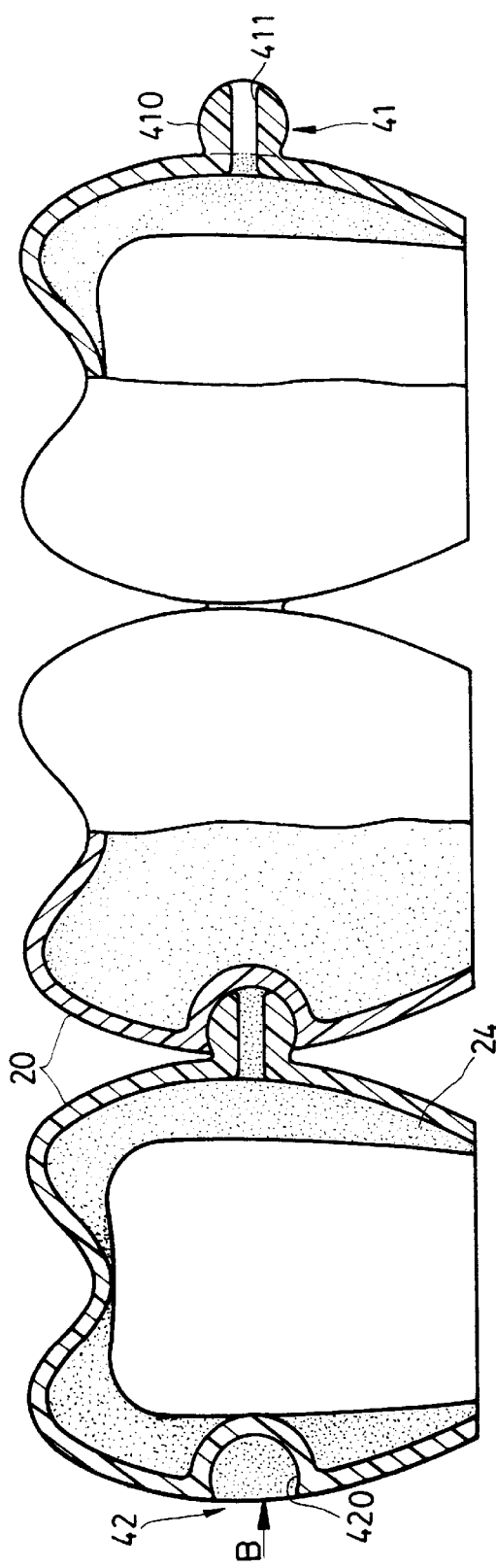
FIG. 4 is a front portion sectional view of the second embodiment of the pre-formed tooth crown in accordance with the present invention.

The invention disclosed herein is directed to a pre-formed tooth crown. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Referring now to FIG. 2 and FIG. 3, the pre-formed tooth crown 2 in accordance with the present invention is a cone shape with an open base. The cone shape is manufactured in various profiles in accordance with human teeth form, the incisors, premolars, or molars. The pre-formed tooth crown 2 has connection means located at both lateral surfaces 20 between two adjacent crowns. The connection means further comprises a male fastener 21 and a corresponding female fastener 22. By providing the male fastener 21 and the female fastener 22, more than three pre-formed tooth crowns 2 can be connected as a crown bridge 2'. By applying the lateral tooth crowns 2a and 2b resting on the teeth 31 and 32 adjacent to the missing tooth 30, the crown bridge 2' can then successfully form temporary imitate teeth.

As illustrated in FIG. 2 and FIG. 3, the male fastener 21 is a hollow mushroom-shaped body 210 rising above the adjacent surface 20. At lateral view as shown in FIG. 3, the mushroom-shaped body 210 is like a booming flower with a central hole 21 1 connecting to the root 212 of the mushroom-shaped body 210 and the inner surface 23 of the tooth crown 2. The female fastener 22, located at the opposing lateral surface 20 of the same tooth crown 2 to the lateral surface 20 where the male fastener 21 located, is concave-shaped as a receiving cavity 220. The receiving cavity 220 is a through hole and has an interior 221 shaped the same as the profile of the mushroom-shaped body 210 of the male fastener 21.

After engaging aforesaid male fastener 21 with the female fastener 22 of the adjacent tooth crown 2, lining material 24 can be used to stuff the interior of the tooth crown 2 and then the stuffed tooth crown can be used as a replacement of a missing tooth. While setting the tooth crown 2 on the abutment, the lining material 24 inside will be squeezed into the receiving cavity 220 of the female fastener 22 via the central hole 211 of the male fastener 21 and the clearance 213 among the booming flower. The lining material 24 in the receiving cavity 220 of the female fastener 22 then bind with the lining material 24 entering the receiving cavity 220 from the other end. By providing the engaging of the male fastener 21 and the female fastener 22, the lining material inside will fill all possible clearance existing in the engagement of multiple tooth crowns 2 for forming a firm binding of the crown bridge 2'.

According to the present invention, the pre-formed tooth crown 2 can be used to form a crown bridge 2', and also can be used individually as a single tooth restoration. In the application as a tooth restoration, the male fastener 21 should be cut away, and the cavities generating from the cut and the receiving cavity 220 of the female fastener 22 will be filled by the lining material 24 inside the tooth crown 2.

Figure 5:
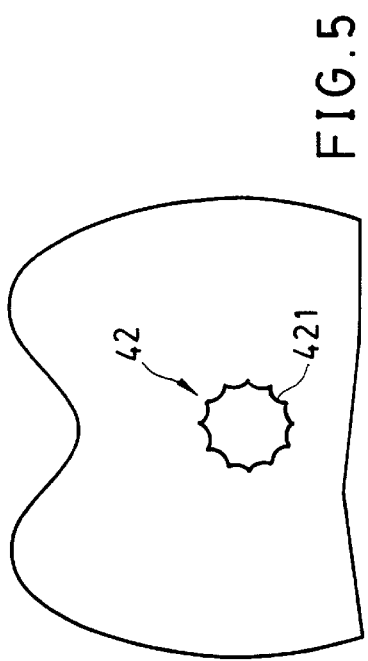
FIG. 5 is a lateral view of the preferred pre-formed tooth crown in accordance with the present invention viewing from point B of FIG. 4.

Referring now to FIG. 4 and FIG. 5, the fastener set can be differently constructed. In the second embodiment of the tooth crown, the male fastener 41, located at one lateral surface 20 of the tooth crown, is a ball-shaped bump 410 with a central hole 411. The female fastener 42 at the opposing lateral surface 20 is concave down as a ball-shaped cavity 420. The ball-shaped cavity 420, at a lateral view, is also like a booming flower 421 as providing the central space for receiving the ball-shaped bump 410 of the male fastener 41. While in engagement of the male fastener 41 and the female fastener 42, the lining material inside the tooth crowns 2 will flow from the central hole 411 of the male fastener 41 into the ball-shaped cavity 420 to further ensure the binding between the male fastener 41 and the female fastener 42.

Figure 6:
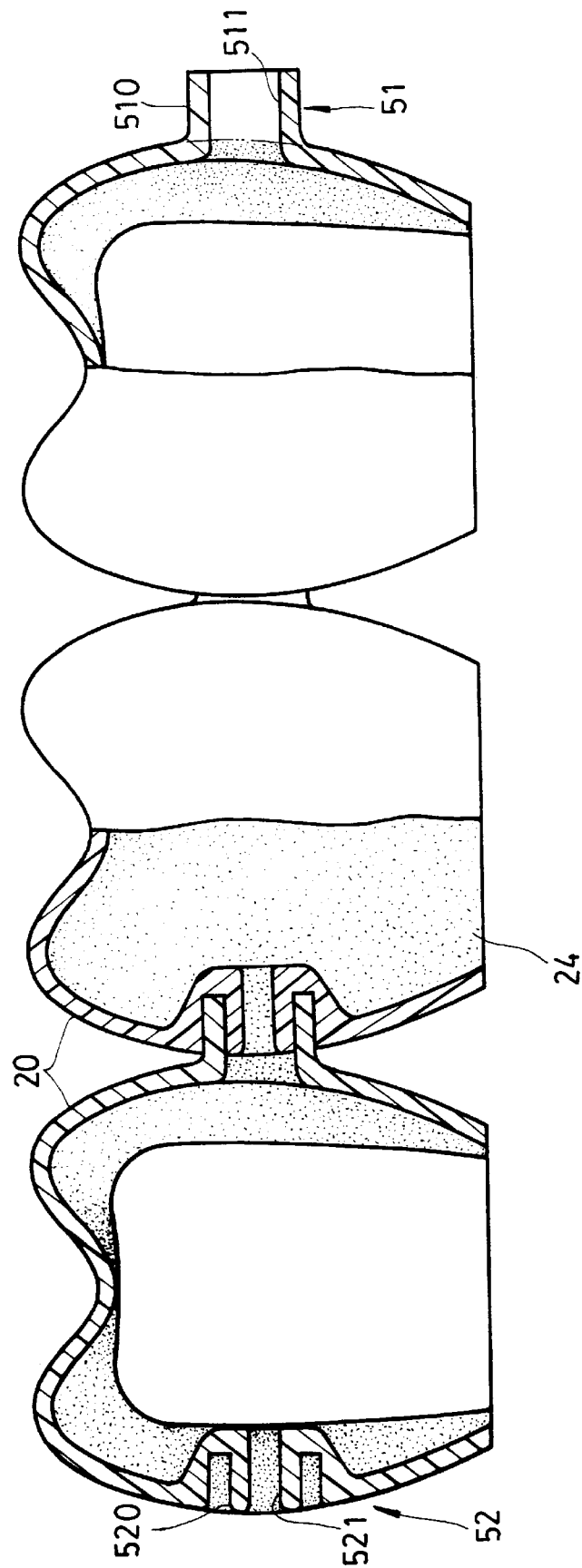
FIG. 6 is a front portion sectional view of the third embodiment of the pre-formed tooth crown in accordance with the present invention.

Referring now to FIG. 6, the fastener set can be differently constructed. In the third embodiment of the tooth crown, the male fastener 51, located at one lateral surface 20 of the tooth crown, is a pipe-shaped bump 510 with a central hole 511. The female fastener 52 at the opposing lateral surface 20 is a ring-shaped groove 520 with a center through hole 521. By plugging the pipe-shaped bump 510 of the male fastener 51 into the ring-shaped groove 520 of the female fastener 52 of another tooth crown, two tooth crowns can be bridged. While in engagement of the male fastener 51 and the female fastener 52, the lining material 24 inside the tooth crowns 2 will flow from the central hole 511 of the male fastener 51 into the central through hole 521 of the female fastener 52 to further ensure the binding between the male fastener 51 and the female fastener 52.

Referring now to FIG. 7 and FIG. 8, the fastener set can be differently constructed. In the fourth embodiment of the tooth crown, the male fastener 61, located at one lateral surface 20 of the tooth crown, is an 8-shaped key 610 with a central hole 611. The female fastener 62 at the opposing lateral surface 20 is a key way 620 with a central through hole 621, for receiving the 8-shaped key 610 of the male fastener 61. By plugging the 8-shaped key 610 of the male fastener 61 into the key way 620 of the female fastener 62 of another tooth crown, two tooth crowns can be bridged. While in engagement of the male fastener 61 and the female fastener 62, the lining material 24 inside the tooth crowns 2 will flow from the central hole 611 of the male fastener 61 into the central through hole 621 of the female fastener 62 to further ensure the binding between the male fastener 61 and the female fastener 62.

Figure 9:
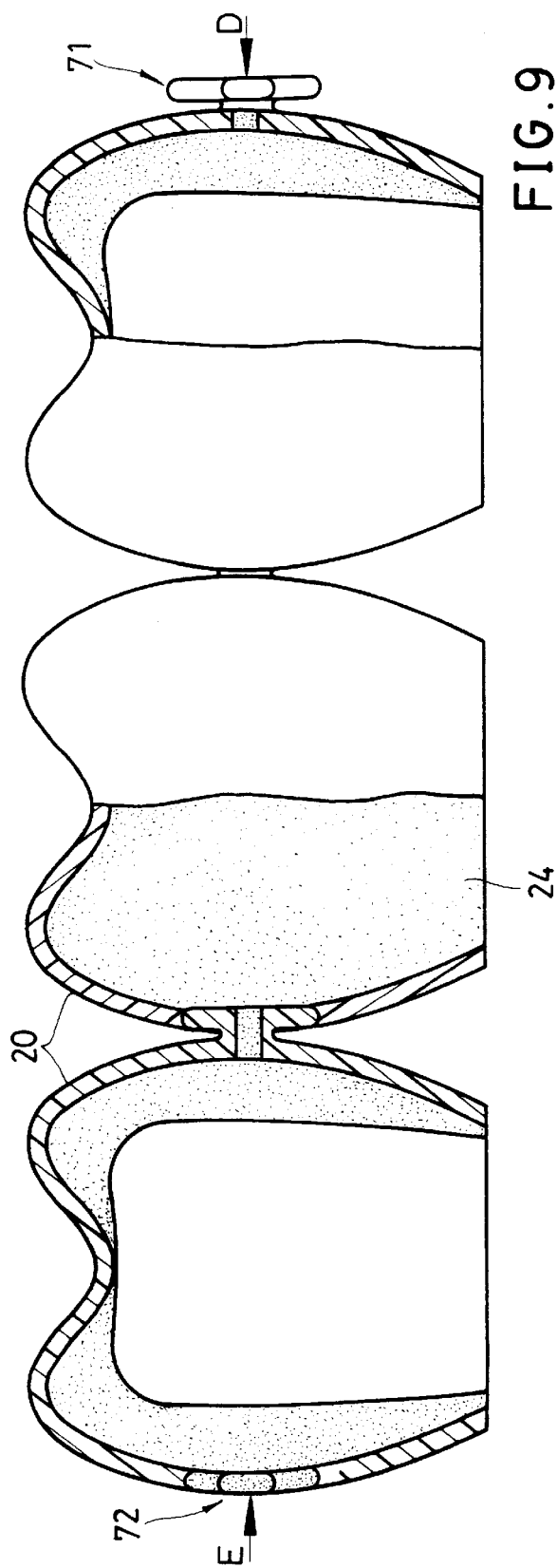
FIG. 9 is a front portion sectional view of the fifth embodiment of the pre-formed tooth crown in accordance with the present invention.
Figure 11:
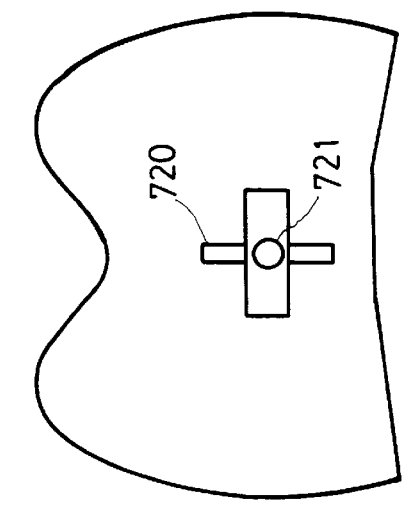
FIG. 11 is a lateral view of the preferred pre-formed tooth crown in accordance with the present invention viewing from point E of FIG. 9.
Figure 10:
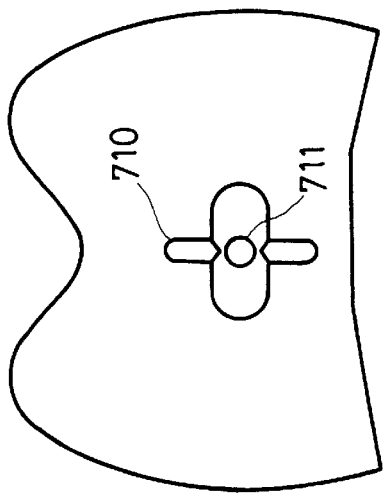
FIG. 10 is a lateral view of the preferred pre-formed tooth crown in accordance with the present invention viewing from point D of FIG. 9.

Referring now to FIG. 9 to FIG. 11, the fastener set can be differently constructed. In the fifth embodiment of the tooth crown, the male fastener 71, located at one lateral surface 20 of the tooth crown, is a cross button 710 with a central hole 711. The female fastener 72 at the opposing lateral surface 20 is a cross socket 720 with a central through hole 721, for receiving the cross button 710 of the male fastener 71. By plugging the cross button 710 of the male fastener 71 into the cross button 720 of the female fastener 72 of another tooth crown, two tooth crowns can be bridged. While in engagement of the male fastener 71 and the female fastener 72, the lining material 24 inside the tooth crowns 2 will flow from the central hole 711 of the male fastener 71 into the central through hole 721 of the female fastener 72 to further ensure the binding between the male fastener 71 and the female fastener 72.

Figure 12:
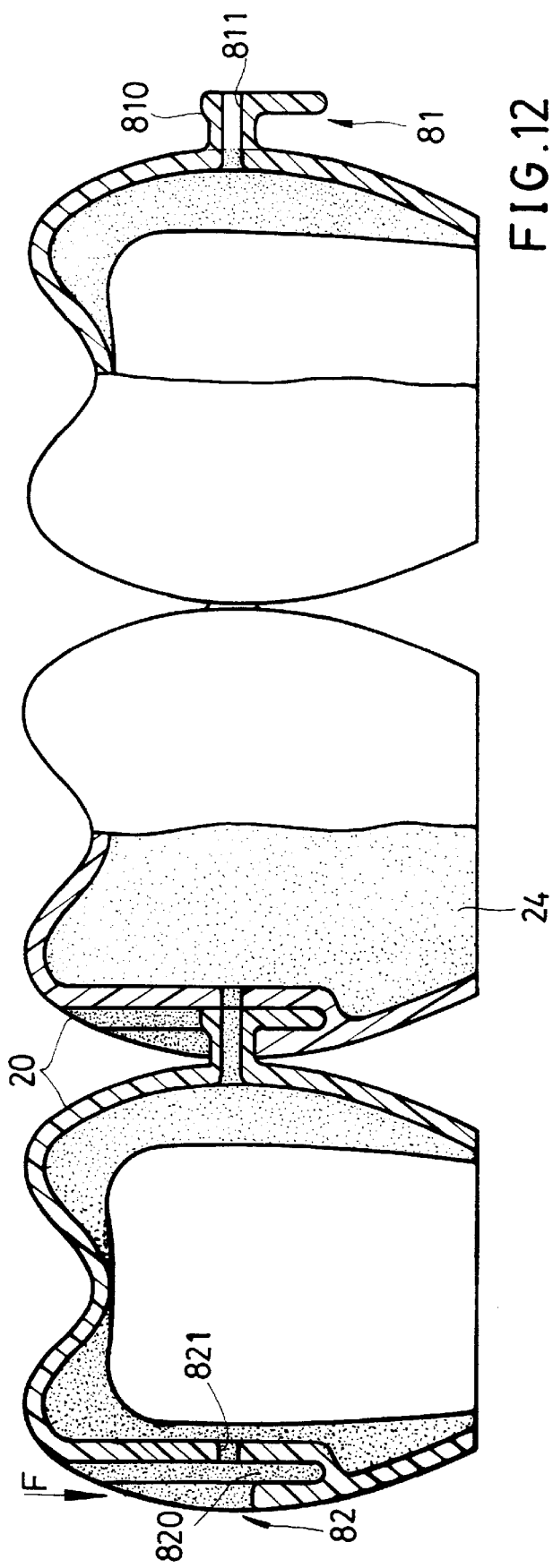
FIG. 12 is a front portion sectional view of the sixth embodiment of the pre-formed tooth crown in accordance with the present invention.
Figure 13:
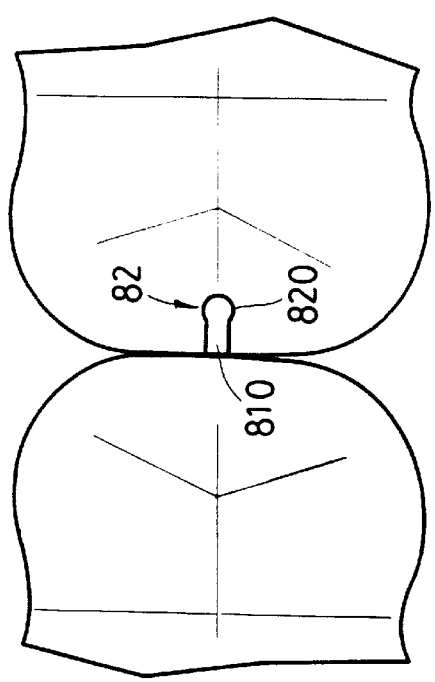
FIG. 13 is a lateral view of the preferred pre-formed tooth crown in accordance with the present invention viewing from point F of FIG. 12.

Referring now to FIG. 12, the fastener set can be differently constructed. In the sixth embodiment of the tooth crown, the male fastener 81, located at one lateral surface 20 of the tooth crown, is a pin 810 with an upper central hole 811. The female fastener 82 at the opposing lateral surface 20 is a pin hole 820 with a upper central through hole 821, for receiving the pin 810 of the male fastener 81. By plugging the pin 810 of the male fastener 81 into the pin hole 820 of the female fastener 82 of another tooth crown, two tooth crowns can be bridged. While in engagement of the male fastener 81 and the female fastener 82, the lining material 24 inside the tooth crowns 2 will flow from the upper central hole 811 of the male fastener 81 into the upper central through hole 821 of the female fastener 82 to further ensure the binding between the male fastener 81 and the female fastener 82.

Figure 15:
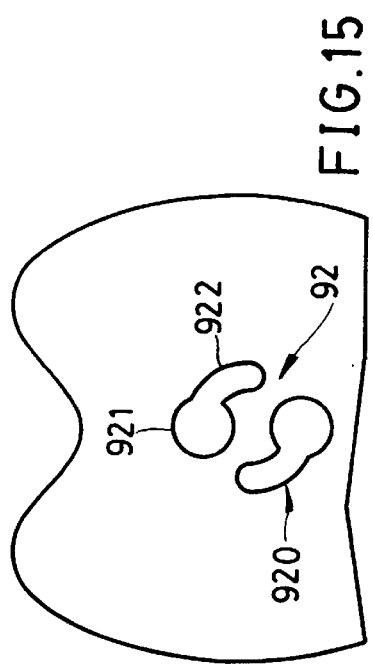
FIG. 15 is a lateral view of the preferred pre-formed tooth crown in accordance with the present invention viewing from point G of FIG. 14.
Figure 14:
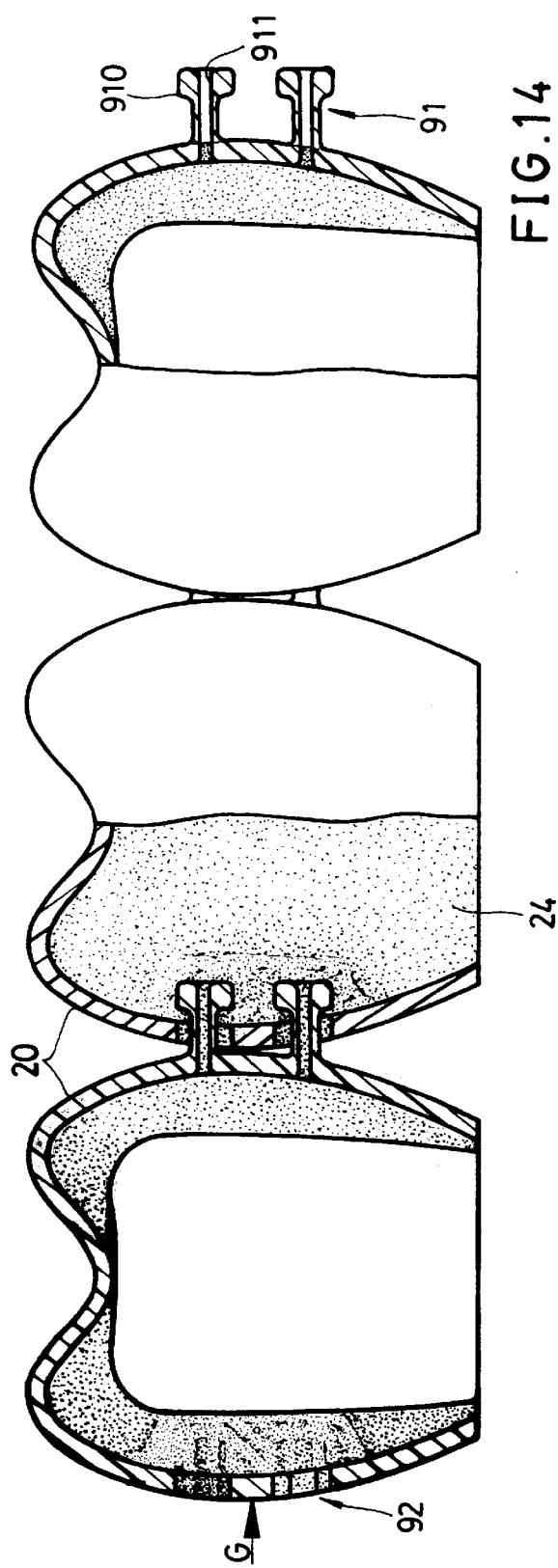
FIG. 14 is a front portion sectional view of the seventh embodiment of the pre-formed tooth crown in accordance with the present invention.

Referring now to FIG. 14 and FIG. 15, the fastener set can be differently constructed. In the seventh embodiment of the tooth crown, the male fastener 91, located at one lateral surface 20 of the tooth crown, is a pair of round-head buttons 910 with individual central holes 911. The female fastener 92 at the opposing lateral surface 20 is a circular cavity 920 with a surface through hole plate 921, for receiving the round-head buttons 910 of the male fastener 91. By plugging the round-head buttons 910 of the male fastener 91 into the circular cavity 920 of the female fastener 92 of another tooth crown through the surface through hole plate 921 and turning the male fastener 91 clockwise for the round-head buttons 910 sit into the cavity hole 922 of the circular cavity 920, two tooth crowns can be bridged. While in engagement of the male fastener 91 and the female fastener 92, the lining material 24 inside the tooth crowns 2 will flow from the central hole 911 of the male fastener 91 into the surface through hole plate 921 of the female fastener 92 to further ensure the binding between the male fastener 91 and the female fastener 92.

Figure 16:
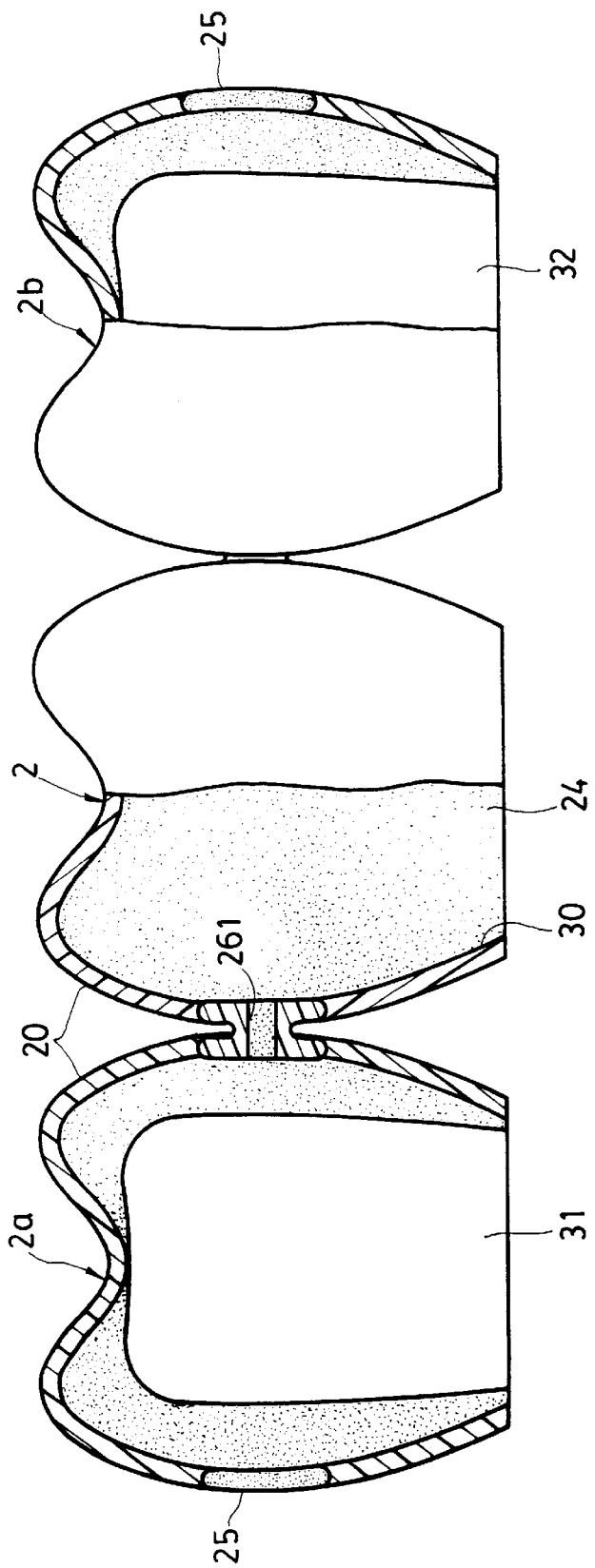
FIG. 16 is a front portion sectional view of another embodiment of the pre-formed tooth crown in accordance with the present invention.
Figure 17:
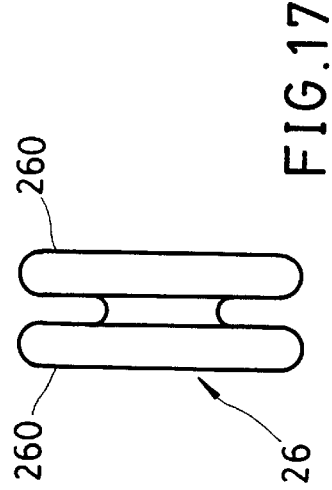
FIG. 17 is a front view of the male fastener of another embodiment of the preformed tooth crown in accordance with the present invention showing in FIG. 16.

Referring now to FIG. 16 and FIG. 17, another embodiment of the tooth crown is shown to have the fastener set differently constructed. In the embodiment, the male fastener 26 is an isolated connector with two parallel side buttons 260 and a central holes 261. The female fastener 25 located one at each the lateral surface 20 is a cavity for receiving the side button 260 of the male fastener 26. By sitting the side buttons 260 of the male fastener 26 into the female fasteners 25 of adjacent tooth crowns at the contact surface, two tooth crowns can then be bridged easily.

While the present invention has been particularly shown and described with reference to preferred embodiments, it will be understood by those skilled in the art that various changes in form and detail may be without departing from the spirit and scope of the present invention.

I claim:

1. A bridge having at least first and second pre-formed tooth crowns, the bridge comprising:

connection means at lateral surfaces of each of the at least two crowns for bridging two adjacent tooth crowns, the connection means including a male fastener at one lateral surface of the first crown and a female fastener at an opposing lateral surface of the second crown, the male fastener being engaged with the female fastener of an adjacent crown whereby the bridge is formed;

a hole provided in the male fastener and a hole provided in the female fastener; and lining material insertable inside the at least first and second tooth crowns, the lining material being squeezed from one tooth crown to the adjacent tooth crown after the bridge is located onto teeth of a patient, the lining material being squeezed through the holes of adjacent fastener to ensure binding within said crown bridge.

2. The bridge as recited in claim 1, wherein each of the crowns have a male fastener and a female fastener.

3. The bridge as recited in claim 1, wherein the holes in the male and female fastener are centrally located.

4. The bridge as recited in claim 1, wherein the connection means is an isolated connector with two side buttons and wherein the male fastener is one of the buttons and the female fastener is a cavity provided in the second crown, one of the side buttons being mountable in the cavity in the second crown.

5. The bridge as recited in claim 4, wherein the two side buttons are parallel and wherein both of the buttons have the hole provided in the male fastener.

6. The bridge as recited in claim 1, wherein the male fastener is a hollow mushroom-shaped body rising above the one lateral surface of the first crown, the mushroom-shaped body having a booming flower-shaped circumference and the hole provided in the male fastener is a centrally located hole in the mushroom-shaped body, and wherein the female fastener is a receiving cavity for accommodating the male fastener of the adjacent tooth crown and the bridge is formed while the male and female fasteners are in engagement.

7. The bridge as recited in claim 1, wherein the male fastener is a ball-shaped body with a booming flower-shaped circumference and the hole provided in the male fastener is a centrally located hole, and wherein the female fastener is a ball-shaped cavity for accommodating said male fastener of the adjacent tooth crown and the bridge is formed while the male and female fasteners are in engagement.

8. The bridge as recited in claim 1, wherein the male fastener is a pipe-shaped body and the hole provided in the male fastener is a centrally located hole, and wherein the female fastener is a ring-shaped groove for accommodating said male fastener of the adjacent tooth crown and the bridge is formed while the male and female fasteners are in engagement.

9. The bridge as recited in claim 1, wherein the male fastener is a figure eight-shaped key and the hole provided in the male fastener is a centrally located hole, and wherein the female fastener is a figure eight-shaped key way for accommodating said male fastener of the adjacent crown and the bridge is formed while the male and female fasteners are in engagement.

10. The bridge as recited in claim 1, wherein the male fastener is a cross button and the hole provided in the male fastener is a centrally located hole, and wherein the female fastener is a cross socket for accommodating the male fastener of the adjacent crown and the bridge is formed while the male and female fasteners are in engagement.

11. The bridge as recited in claim 1, wherein the male fastener is a pin and the hole provided in the male fastener is a centrally located upper hole, and wherein the female fastener is a pin hole for accommodating the male fastener of the adjacent crown and the bridge is formed while the male and female fasteners are in engagement.

12. The bridge as recited in claim 1, wherein the male fastener includes a plurality of round-head buttons and the hole provided in the male fastener is an individual central hole in each of the buttons, and wherein the female fastener includes a round cavity with a surface through hole plate, the surface through hole plate having a pair of holes for receiving the round-head buttons and the bridge being formed while the male and female fasteners are in engagement.

* * * * *